United States Patent
Swital et al.

(10) Patent No.: US 9,993,150 B2
(45) Date of Patent: Jun. 12, 2018

(54) MONITORING SYSTEM FOR MONITORING HEAD MOUNTED DEVICE WEARER

(71) Applicant: ESSILOR INTERNATIONAL (COMPAGNIE GENERALE D'OPTIQUE), Charenton-le-Pont (FR)

(72) Inventors: Marion Swital, Charenton-le-Pont (FR); Benoit Callier, Charenton-le-Pont (FR); Thierry Villette, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days. days.

(21) Appl. No.: 15/311,275

(22) PCT Filed: May 15, 2015

(86) PCT No.: PCT/EP2015/060755
§ 371 (c)(1),
(2) Date: Nov. 15, 2016

(87) PCT Pub. No.: WO2015/173388
PCT Pub. Date: Nov. 19, 2015

(65) Prior Publication Data
US 2017/0188807 A1 Jul. 6, 2017

(30) Foreign Application Priority Data

May 15, 2014 (EP) .................................... 14305717
Jun. 9, 2014 (EP) .................................... 14305868

(51) Int. Cl.
*A61B 3/14* (2006.01)
*A61B 3/00* (2006.01)
(Continued)

(52) U.S. Cl.
CPC ............ *A61B 3/0025* (2013.01); *A61B 3/113* (2013.01); *A61B 5/0004* (2013.01); *A61B 5/165* (2013.01);
(Continued)

(58) Field of Classification Search
CPC ....... A61B 3/113; A61B 3/0025; A61B 3/112; G06K 9/00604; G06F 3/013
(Continued)

(56) References Cited

U.S. PATENT DOCUMENTS 9,516,283 B2 * 12/2016 Hilkes .................... H04N 7/185
2005/0088616 A1 * 4/2005 Nason .................... G02C 7/027
351/159.74

(Continued)

FOREIGN PATENT DOCUMENTS

| WO | 2008055262 A2 | 5/2008 |
| WO | 2011153112 A2 | 8/2011 |
| WO | 2014001494 A1 | 1/2014 |

OTHER PUBLICATIONS

International Search Report, dated Feb. 29, 2016, from corresponding PCT Application.

*Primary Examiner* — Mohammed Hasan
(74) *Attorney, Agent, or Firm* — Young & Thompson (57) ABSTRACT

A monitoring system for monitoring the visual behavior of a wearer of a head-mounted device, the monitoring system includes: —a least one wearer's visual behavior sensor configured to sense at least one wearer's visual behavior data relating to the visual behavior of the wearer of the head-mounted device, —a communication unit associated with the at least one wearer's visual behavior sensor and configured to communicate the visual behavior data to a wearer information data generating unit, —a wearer information data generating unit configured to: —receive the wearer's visual behavior data, —store the wearer's visual (Continued)

behavior data, and —generate an wearer information data indicative of at least one of: wearer's vision or general health condition of the wearer or wearer's activity or wearer's authentication based, at least, on the evolution over time of the wearer's visual behavior data.

19 Claims, 4 Drawing Sheets

(51) Int. Cl.
| | | |
|---|---|---|
| *G02B 27/01* | (2006.01) | |
| *A61B 3/113* | (2006.01) | |
| *A61B 5/16* | (2006.01) | |
| *A61B 5/00* | (2006.01) | |
| *G06F 19/00* | (2018.01) | |
| *G06F 21/31* | (2013.01) | |
| *G06Q 30/06* | (2012.01) | |

(52) U.S. Cl.
CPC ....... *G02B 27/017* (2013.01); *G06F 19/3406* (2013.01); *G06F 21/316* (2013.01); *G06Q 30/0635* (2013.01); *G02B 2027/014* (2013.01); *G02B 2027/0138* (2013.01); *G02B 2027/0141* (2013.01)

(58) Field of Classification Search
USPC .................................................. 351/200–246
See application file for complete search history.

(56) References Cited

U.S. PATENT DOCUMENTS

2013/0242262 A1* 9/2013 Lewis ................ G02B 27/0093
351/209
2016/0302663 A1* 10/2016 Fayolle .................. A61B 3/113

* cited by examiner

MONITORING SYSTEM FOR MONITORING HEAD MOUNTED DEVICE WEARER

TECHNICAL FIELD

The invention relates to a monitoring system for monitoring the visual behavior of a wearer of a head-mounted device and a method for monitoring the vision of a wearer using a head mounted device with a monitoring system according to the invention.

BACKGROUND OF THE INVENTION

The discussion of the background of the invention herein is included to explain the context of the invention. This is not to be taken as an admission that any of the material referred to was published, known or part of the common general knowledge at the priority date of any of the claims.

Usually, an eyewear equipment wearer wishing to have an eyewear equipment goes to see an eye care practitioner.

The eye care practitioner may carry out a number of tests to determine the most appropriate eyewearer equipment for the wearer.

The period of time between two visits of a wearer to his eye care practitioner may be long, for example a year or more.

The tests carried out by the eye care practitioner are usually in specific conditions and over short periods of times. Furthermore the tests only cover part of the very different visual situation the wearer may face. Therefore, the eyewear equipment settings correspond to the best average compromise between the different visual situations the wearer may face based on the visual test carried out at a given point in time.

Since the visual requirements of a wearer may change over time or depending on the visual situation, there is a need for a system and a method for providing information concerning the visual behavior of the wearer in all type of visual situation.

An aim of the present invention is to propose a system for monitoring the visual behavior of a wearer of a head-mounted device.

SUMMARY OF THE INVENTION

To this end, the present invention relates to a monitoring system for monitoring the visual behavior of a wearer of a head-mounted device, the monitoring system comprises:
  a least one wearer's visual behavior sensor configured to sense at least one wearer's visual behavior data relating to the visual behavior of the wearer of the head-mounted device,
  a communication unit associated with the at least one wearer's visual behavior sensor and configured to communicate said visual behavior data to a wearer information data generating unit,
  a wearer information data generating unit configured to:
  receive said wearer's visual behavior data,
  generate an wearer information data indicative of at least one of: wearer's vision or general health condition of the wearer or wearer's activity or wearer's authentication based, at least, on the evolution over time of said wearer's visual behavior data.

Advantageously, the monitoring system of the invention allows from the monitoring of the visual behavior of the wearer to generate a wearer information data. The monitoring system further allows monitoring the visual behavior of the wearer over a great variety of visual situations and very regularly, even in a continuous manner.

According to further embodiments which can be considered alone or in combination:
  the wearer information data generating unit is configured to generate wearer information data using statistical analysis of said at least one wearer's visual behavior data received and stored over time; and/or
  the wearer information data generating unit is a distant entity from the head mounted device, the wearer information data generating unit being further arranged to communicate with sensors associated to a plurality of head-mounted devices; and/or
  the information data generating unit is configured to receive wearer's visual behavior data relating to a plurality of wearers and wherein said generated wearer information data is based, at least, on said wearer's visual behavior data relating to a plurality of wearer's; and/or
  the information data generating unit is configured to receive wearer's visual behavior data relating to a plurality of wearers and to generate statistical information based on said data and generate an information indicative of wearer visual behavior over time for a specific wearer based on said statistic information; and/or
  the generated wearer information data are indicative of human emotions and/or affective states of the wearer.
  the wearer information data generating unit is configured to provide a recommendation data based, at least, on at least one of the wearer's visual behavior data or the generated wearer information data; and/or
  the recommendation data includes a lens design recommendation and/or an ophthalmic lens recommendation and/or an alert indicative of wearer's vision state and/or an activation of at least one functionality on the head mounted device and/or an access to a service offer; and/or
  the monitoring system is used for early detection of events occurring around a wearer;
  the sensor is associated with the head mounted device; and/or
  the head mounted device comprises the at least one wearer's visual sensor and the communication unit, and wherein the data generating unit is external to the head mounted device; and/or
  the wearer information data generating unit is arranged to send the wearer information data to a wearable computer device, a personal computer device and/or a smart building device associated to the wearer of the head mounted device; and/or
  the monitoring system is further configured to send to a printing unit a printing request based on information indicative of the generated wearer information, and wherein the printing request causes said printing unit to print an object representative of the generated wearer information; and/or
  the monitoring system further comprising an optical function controller adapted to control the optical function of the head-mounted device, and wherein the wearer's visual behavior data comprise at least one optical parameter of the optical function of the head mounted device
  the sensor is adapted to measure at least one wearer environment parameter; and/or
  the head mounted device comprises a camera adapted to acquire images of the environment of the wearer and a display device adapted to display to the wearer virtual images in addition to the real scene seen through the head mounted device, the virtual images depending on the images acquired by the camera, the optical parameter comprising at least parameter relating to the image processing applied to the virtual images prior to being displayed to the wearer; and/or the head mounted device further comprises a display device configured to display virtual images to the user and wherein upon reception of an information indicative of the generated wearer information by the head mounted device, the display device is further configured to display a virtual image indicative of said information indicative of the generated wearer information; and/or the optical parameter of the optical function comprises at least a transmission parameter of the head mounted device; and/or the head-mounted device further comprising an eye tracking device adapted to track the gazing direction of the wearer, and wherein the wearer's visual behavior data comprise at least oculomotor parameter data relating to the oculomotor behavior of the wearer determined using the eye tracking device.

The invention also relates to a method for monitoring the vision of a wearer using a head mounted device with a system according to the invention, the method comprising:

a wearer visual behavior data sensing step S1 during which wearer visual behavior data are sensed and sent to the data generating unit, a wearer visual behavior data receiving step S4 during which wearer visual behavior data are received by the data generating unit;

an information generating step S6, during which the data generating unit generates an information indicative of wearer visual behavior over time based at least on the wearer visual behavior data, wherein the wearer visual behavior data sensing step S1 and the wearer visual behavior data receiving step S4 are repeated over time.

According to further embodiments which can be considered alone or in combination:

the method further comprising a recommendation providing step S7 during which the data generating unit provides a recommendation relative to the vision of the wearer, said recommendation being based at least on the information indicative of the evolution of the wearer visual behavior over time; and/or the head mounted device comprises at least one sensor adapted to measure at least one visual environment parameter of the visual environment of the wearer, and an optical function controller adapted to control the optical function of the head-mounted device, the method further comprises for at least one optical parameter of the optical function of the head mounted device:

during the wearer visual behavior data sensing step S1, an optical function adapting substep S1a, during which the optical parameter of the optical function is adapted and an optical parameter recording substep S1b, during which the value of the optical parameter of the optical function is recorded, a visual environment parameter measuring step S2, during which at least one visual environment parameter is measured upon the optical function adapting step S1a, a referential optical parameter determining step S3, during which a referential optical parameter is determined based on the measured value of the at least one visual environment parameter and wearer data, wherein steps S1 to S4 are repeated over time and during the information generating step S6, the evolution of the difference between the referential optical parameter and the optical parameter is checked over time; and/or the method further comprising the recommendation providing step S7 during which a recommendation is trigged when the difference between the referential optical and the optical parameter is greater than a threshold value; and/or the head mounted device comprises a camera adapted to acquire images of the environment of the wearer and a display device adapted to provide to a user virtual images in addition to the real scene seen through the head mounted device, the virtual images depending on the images acquired by the camera, wherein during the optical function adapting step an image processing is applied to the virtual images prior to being displayed to the wearer; and/or the image processing comprises at least a magnification processing; and/or the image processing comprises at least a contrast enhancement processing and/or a detail enhancement processing and the visual environment parameter relates to the visual environment contrast and/or the visual environment color contrast and/or luminosity of the visual environment; and/or the optical parameter relates to the luminosity of the display device and the visual environment parameter relates to the luminosity of the visual environment; and/or the head-mounted device further comprises an eye tracking device adapted to track the gazing direction of the wearer, and wherein the method further comprises:

during the wearer visual behavior data sensing step S2, an oculomotor parameter determining step during which a oculomotor parameter relating to the oculomotor behavior of the wearer is determined using the eye tracking device, and an oculomotor parameter recording step during which the value of the oculomotor parameter is recording, and during the indication of wearer visual behavior evolution over time generating step S6, the evolution of the oculomotor parameter is checked overtime; and/or the oculomotor parameter is used to determine the reading speed of the wearer, the evolution of the reading speed of the wearer is checked over time; and/or the wearer data comprise at least a visual parameter comprising at least the optical prescription of the wearer; and/or during the optical function adapting step S1, the transmission of the head mounted device is adapted and the visual environment parameter measuring during the visual environment parameter measuring step S3 corresponds to the light spectrum and/or light intensity of the visual environment.

According to a further aspect, the invention relates to a computer program product comprising one or more stored sequences of instructions that are accessible to a processor and which, when executed by the processor, causes the processor to carry out the steps of the method according to the invention.

The invention further relates to a computer readable medium carrying one or more sequences of instructions of the computer program product according to the invention.

Furthermore, the invention relates to a program which makes a computer execute the method of the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

BRIEF DESCRIPTION OF THE DRAWINGS

Other features and advantages of the present invention will become apparent from the following description of non-limitative embodiments, with reference to the attached drawing in which.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

DETAILED DESCRIPTION OF EMBODIMENTS OF THE INVENTION

Figure 1:
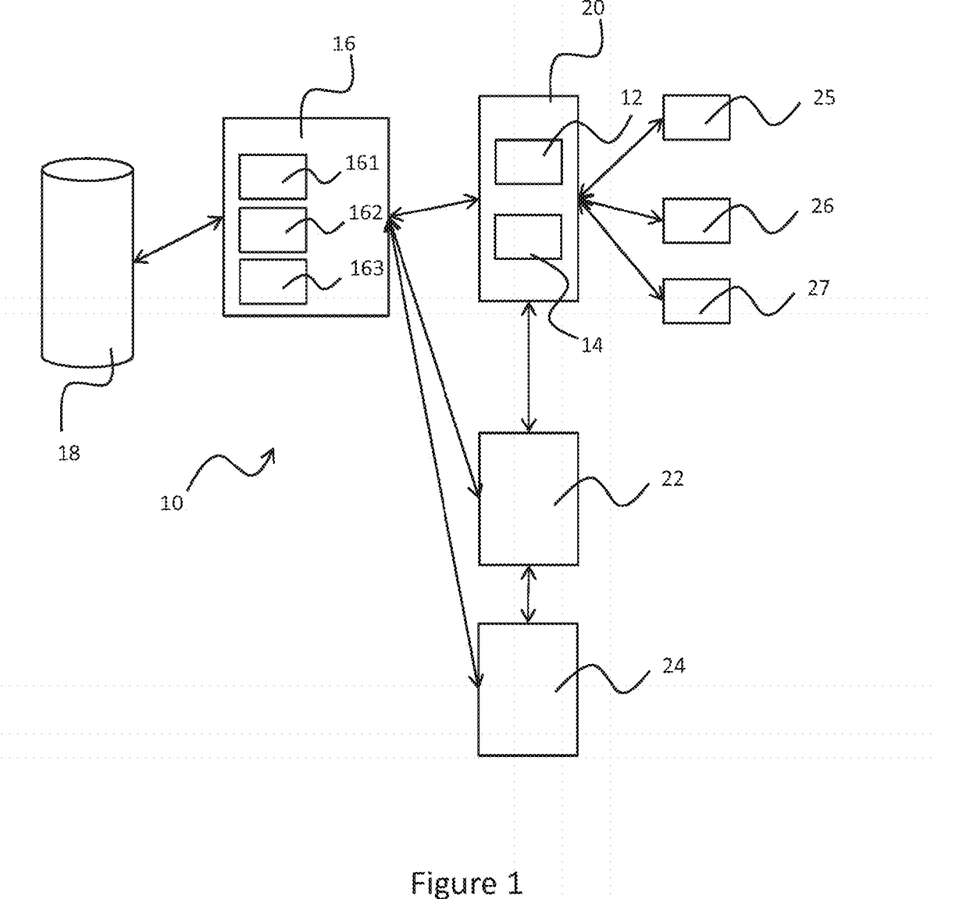
FIG. 1 is an illustration of a block diagram of an exemplary non-limiting monitoring system according to an embodiment of the invention.

FIG. 1, illustrates a monitoring system 10 according to a first embodiment of the invention.

The monitoring system 10 illustrated on FIG. 1, is arranged for monitoring the visual behavior of a wearer of a head-mounted device 20.

The monitoring system 10 comprises at least one wearer's behavior sensor 12, a communication unit 14 and a wearer information data generating unit 16.

The wearer's behavior sensor 12 is configured to sense at least one wearer's visual behavior parameter relating to the visual behavior of the wearer of the head-mounted device 20.

The wearer's behavior sensor 12 may be of any type of sensor that allows measuring wearer's visual behavior parameters so as to obtain wearer's visual behavior data.

The wearer's visual behavior data may comprise wearer's eye data relating to one or both of the eyes of the wearer such as blinking frequency, pupil size, gazing direction, eye expression, eye strain, and/or to oculomotor parameters. The wearer's visual behavior data may further comprise head-mounted device use data relating to the way the wearer uses the head-mounted device, such as the use of a magnification function, the use of a contrast enhancement process or of any image processing available on the head-mounted device.

According to an embodiment of the invention, the sensor may be further adapted to measure at least one visual environment parameter relating to the environment of the wearer of the head mounted device. For example, the ambient brightness may be measured by the sensor.

In the embodiment represented on FIG. 1, the wearer's behavior sensor 12 is part of the head mounted device 20. However, the invention is not limited to such configuration and according to some embodiments of the invention the wearer's behavior sensor 12 may not be part of the head-mounted device. The wearer's behavior sensor 12 may be a remote sensor, for example part of a computer screen or smartphone or a tablet computer.

Furthermore, the monitoring system 10 may comprise a plurality of wearer's behavior sensors 12, each of which may or may not be part of the head mounted device.

The monitoring system further comprises at least one communication unit 14 associated with the at least one wearer's visual behavior sensor 12. The communication unit 14 is configured to communicate the visual behavior data to a wearer information data generating unit 16.

Depending on the configuration of the monitoring system, when the monitoring system comprises a plurality of sensors 12, each sensor 12 may be associated to a communication unit 14 or different sensors 12 may use the same communication unit 14.

The communication unit 14 is arranged at least to send wearer's visual behavior data to the wearer information data generating unit 16. However, the communication unit 14 may further be arranged to send other type of data to the wearer information data generating unit 16 or distinct entities.

The communication unit 14 may further be arranged to receive data from the wearer information data generating unit 16 or distinct entities such as wearable computer device, personal computer device and/or smart building device.

As illustrated on FIG. 1, the distinct entity may comprise other head-mounted devices 22, 24. For example, the other head-mounted device 22 and 24 are used by other wearers located, for example, in the same geographic zone as the wearer of the head-mounted device 20.

The distinct entities may further comprise wearable device that the wearer may be carrying with him, for example a smartphone 25, a tablet 26, a PDA, a smart watch 27 or any other electronic device the wearer may be carrying with him or that may be located at short distant from the wearer, for example at a few meters, such as in the same room or environment as the wearer.

The wearer information data generating unit 16, is configured to receive the wearer's visual behavior data, and to generate an wearer information data based at least on the analysis of said wearer's visual behavior data measured over a certain period of time.

The period of time over which said at least wearers' visual behavior data is measured depends on the type of wearer's visual behavior parameter and on the application of the method. The analysis may be performed on wearers' visual behavior data measured over a short period of time, for example of from 1 second to a few minutes or over longer period of time, like, for example, days, weeks, months or even years.

The wearer information data generated by the wearer information data generating unit 16, are indicative of at least one of: wearer's vision and/or general health condition of the wearer, for example the level of fatigue of the wearer or humans emotions and/or affective states of the wearer, and/or the wearer's activity, for example the fact that wearer is reading, driving, walking, and/or wearer's authentication.

As illustrated on FIG. 1, the wearer information data generating unit 16 is a computing unit that may comprise, but is not limited to, a processing unit 161, a system memory 162, and a system bus 163 that couples various system components including the system memory to the processing unit.

The system memory 162 can include computer storage media in the form of volatile and/or nonvolatile memory such as read only memory (ROM) and/or random access memory (RAM). By way of example, and not limitation, memory 162 can also include an operating system, application programs, other program components, and program data.

The wearer information data generating unit 16 operates in a networked or distributed environment using logical connections to one or more other remote entities, such as wearer's visual behavior sensors 12 and/or wearable computer devices such as a head mounted device, a smart phone, a smart watch and/or personal computer device such as laptop, computer, server system and/or a smart building device such as light adjustment device, home automation devices and/or any further remote device.

The remote device can be a personal computer, a server, a router, a network PC, a peer device or other common network node, or any other remote media consumption or transmission device, and can include any or all of the elements described above relative to the wearer information data generating unit 16. The logical connections depicted in FIG. 1 include a network, such local area network (LAN) or a wide area network (WAN), but can also include other networks/buses e.g., cellular networks.

A user, for example a lens professional or lens designer, can enter commands and information into the wearer information data generating unit 16 through input devices such as keyboard, keypad, a pointing device, a mouse, stylus, touchpad, touch screen, motion detector, camera, microphone or any other device that allows a user to interact with the wearer information data generating unit 16.

A monitor or other type of display device can be also connected to the system bus 163 via an interface, such as output interface. In addition to a monitor, the wearer information data generating unit 16 can also include other peripheral output devices such as speakers and a printer, which can be connected through an output interface.

According to an embodiment of the invention, the monitoring system may also include a storing device 18 configured to store data sensed by the sensor 12 and/or the information generated by the wearer data generating unit 16, for example, statistical information and/or software/computer program related to services.

According to an embodiment, each wearer and/or head mounted device and/or sensor and/or associated remote device or entities may be identified by specific identification data. The identification data may be stored in the storing device. Furthermore, associations of wearers with head mounted devices and/or sensors and/or associated devices can be stored in the storing device 18.

The storing device 18 can also perform various different primary functions (e.g., a smart phone, laptop or head-mounted display device that performs communication, word processing and/or display functions in addition to storage of information or statistical information). While the wearer data generating unit 16 is shown as a separate component from the storing device 18, in some aspects, the wearer data generating unit 16 can included the storing device 18. In some aspects, the wearer data generating unit 16 can be included in the head mounted device 20. According to an embodiment of the invention, the wearer information data generating unit is a distant entity from the head mounted device, the wearer information data generating unit being further arranged to communicate with sensors associate to a plurality of head-mounted devices.

According to an embodiment of the invention, the wearer information generating unit is configured to generate wearer information data, for example but not limited to, statistical information based at least on the wearer visual behavior data analysis. The analysis can be, for example, a statistical analysis.

Statistics involves the collection, organization, analysis, interpretation, and/or presentation of measured/collected information. With advances in technology, more extensive and complex computing allows massive amounts of data to be collected, stored and/or processed. Further, methods for evaluating the data are numerous.

Statistical analysis can be employed to process and/or evaluate data sensed by the sensor 12. The two main types of statistics are descriptive and inferential statistics.

Descriptive statistics includes methods for organizing and summarizing collected data. These methods include, but are not limited to, graphs, tables, charts and measurements such as averages, percentiles, and measures of variation of the data. Data mining for pattern detection, machine learning and artificial intelligence methods, regression modeling and summary statistics can be employed in descriptive statistics.

Inferential statistics is based on methods for making conclusions about data collected based on the evaluation of a sample of the data. For example, predictions can be made regarding the entire set of data. An example prediction can relate to the likelihood that a disease or illness exists based on data collected. Recommendations can be made to achieve or avoid predictions.

Statistical methods such as regression analysis can be employed to analyze data. Regression analysis includes techniques for analyzing different variables to determine the relationship between one or more dependent variables and independent variables. For example, the analysis can be employed to determine how the value of a dependent variable changes when a value of one independent variable changes while keeping the values of other independent variables constant. Regression analysis can be employed for prediction and overlaps with the field of machine learning (a branch of artificial intelligence that employs algorithms to identify patterns in data and/or make predictions based on evaluated data).

Different models can be employed in regression analysis to model the relationship between two variables. Linear regression is a type of regression analysis. Linear regression models the relationship between a dependent variable and an independent variable using linear predictor functions. Unknown model parameters are estimated from the data on which linear regression is performed. Interpolation methods can be employed to perform prediction based on values within the set of collected data used for model-fitting while extrapolation can be employed to perform prediction based on values outside the set of collected data.

In linear regression models, the conditional mean of an independent variable given the dependent variable value is typically an affine function. In some cases, the median, or some other quantile of the conditional distribution of the independent variable given the dependent variable is a linear function of the dependent variable.

Non-linear regression is a type of regression analysis in which observed information is modeled by a non-linear function. The non-linear function is a combination of the model parameters and depends on an independent variable.

According to an aspect of the invention, the wearer data generating unit 16 may be configured to receive wearer's visual behavior data relating to a plurality of wearers and said generated wearer information data is based, at least, on said wearer's visual behavior data relating to a plurality of wearer's.

Figure 2:
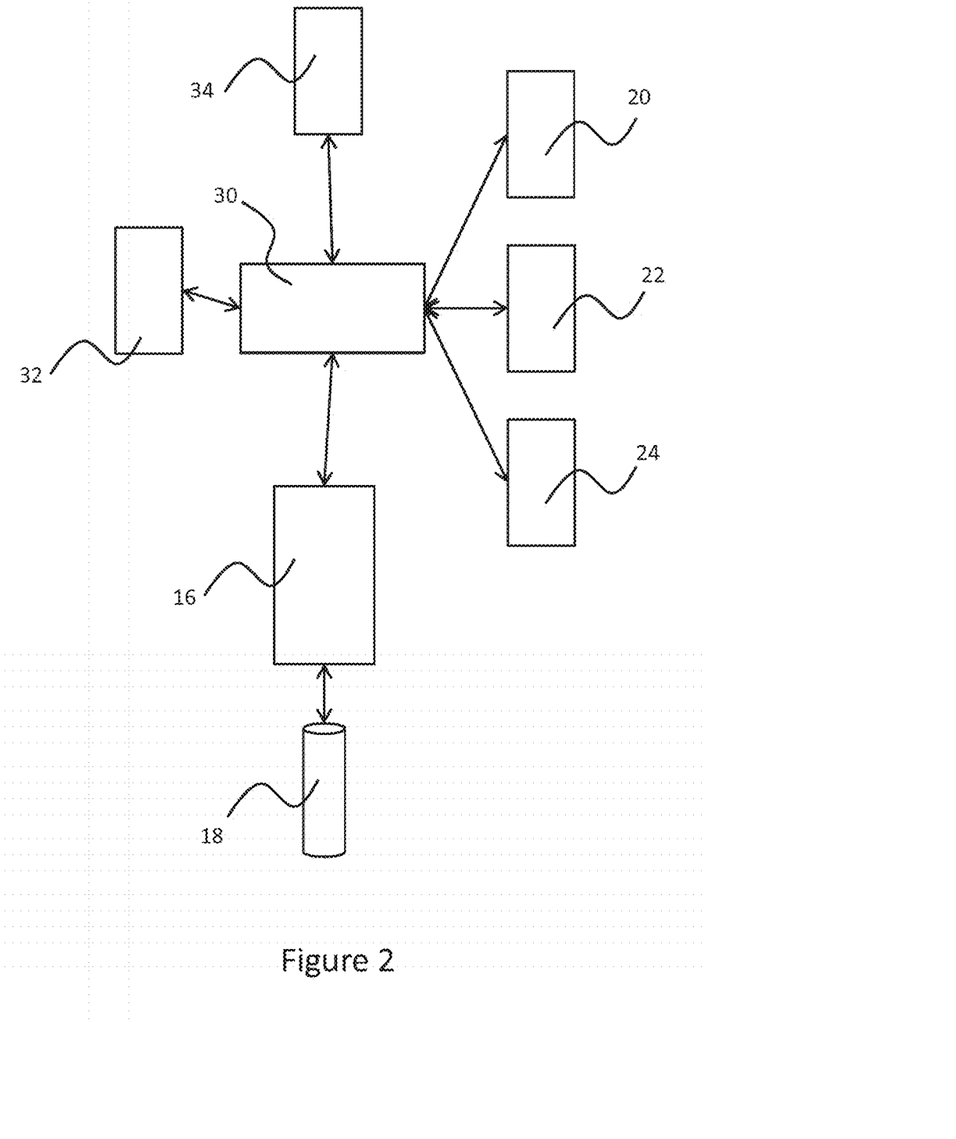
FIG. 2 is an illustration of a block diagram of an exemplary non-limiting monitoring system according to an further embodiment of the invention.

FIG. 2 is an example of a network that allows having the wearer data generating unit 16 receive wearer's visual behavior data from a plurality of sensors associated with head mounted devices.

The network illustrated in FIG. 2, includes head mounted devices 20, 22, 24, etc, at least one wearer data generating unit 16, and computing entities 32, 34 etc. . . .

The computing entities can include programs, methods, data stores, programmable logic, etc.

It can be appreciated that the computing entities can include different devices, such as smart phones, smart watches, personal digital assistants (PDAs), audio/video devices, mobile phones, MPEG-1 Audio Layer 3 (MP3) players, personal computers, laptops, tablets, etc.

Each of the head mounted devices, wearer data generating unit 16, and computing entities can communicate with one or more other by way of the communications network 30, either directly or indirectly. Even though illustrated as a single element in FIG. 2, network 30 can include other computing objects and computing devices that provide services to the system of FIG. 2, and/or can represent multiple interconnected networks, which are not shown.

In a network environment in which the communications network/bus 30 can be the Internet, the wearer data generating unit 16, and computing entities may comprise web servers, file servers, media servers, etc. with which a client computing entity may communicate via any of a number of known protocols, such as the hypertext transfer protocol (HTTP).

According to an arrangement as illustrated on FIG. 2, the wearer data generating unit 16 may generate information data, for example statistical information, based on said wearer's visual data analysis relating to a plurality of wearer's. The wearer data generating unit 16 may generate information indicative of the wearer visual behavior over time for a specific wearer based on the statistic information. The generation of information can be done, for example, by using statistical analysis algorithms.

Furthermore, the wearer data generating unit 16 may be arranged to send the wearer information data to the head mounted device of the wearer or to a computing entity associated with the head mounted device of the wearer.

In an embodiment, the head mounted device further comprises a display device configured to display virtual images to the user and wherein upon reception of an information indicative of the generated wearer information by the head mounted device, the display device is further configured to display a virtual image indicative of said information indicative of the generated wearer information.

According to an embodiment of the invention, the wearer information data generating unit may be configured to further provide a recommendation data based, at least, on at least one of: wearer's visual behavior data or the generated wearer information.

The recommendation data may relate to the vision of the wearer.

For example, recommendation data includes a lens design recommendation and/or an ophthalmic lens recommendation and/or an alert indicative of wearer's vision state and/or an activation of at least one functionality on the head mounted device and/or an access to a service offer. The service offer may relate to wearer's vision and/or the wearer's general health condition, the wearer's activity and/or the wearer's identification and/or the wearer's environment and/or also postural recommendations such as to draw away from one element of the stage or screen, or activity of the wearer such as taking a break or removing the head mounted device.

The wording "lens design" is a widely used wording known from the man skilled in the art in ophthalmic domain to designate the set of parameters allowing to define a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extrafoveal vision, binocular vision and to minimize unwanted astigmatisms. For example, a progressive lens design comprises:

a power profile along the main gaze directions (meridian line) used by the lens wearer during day life activities, distributions of powers (mean power, astigmatism, . . . ) on the sides of the lens, that is to say away from the main gaze direction.

These optical characteristics are part of the "designs" defined and calculated by ophthalmic lens designers and that are provided with the progressive lenses.

In a first example, when a sleepy state of the wearer is detected, the service offer provided may be a search of the nearest rest stop and the suggestion to take a break or the triggering of a remote voice guidance to check that everything is fine for the wearer.

In a second example, when a sleepy state of the wearer is detected during reading or watching videos/television or internet activity, the wearer information data generating unit can provide a suggestion to take a break or to wear eyewear to rest the eyes.

In a third example, if the wearer information data generating unit identifies during reading that the wearer stumbles over words or tires on a word, the service offer provided may be to suggest reading assistance for example, vocal reading assistance or remote reading assistance by a third party.

In another example, if the wearer information data generating unit does not identify any reaction of the eye (no blinking, no movement of the eye for example), an alert may be triggered by calling the emergency teams, optionally sending them the geolocalization fo the wearer and the wearer information data related to the health or the vision of the wearer. In an embodiment, further checking of the wearer may be triggered such as pulse and/or temperature measurements.

Figure 3:
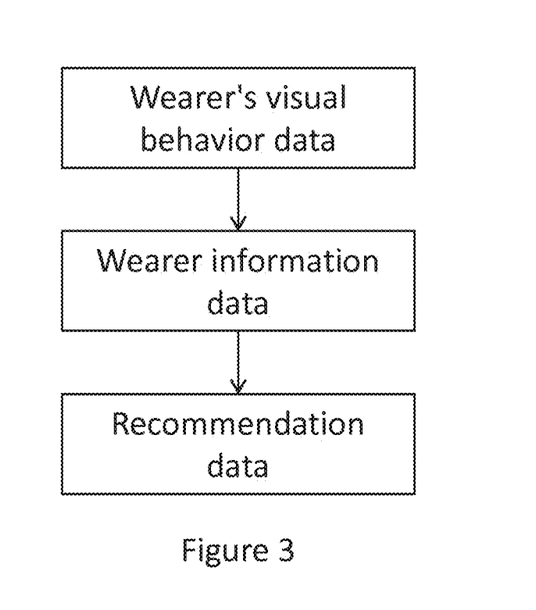
FIG. 3 is an illustration of a block diagram of the transfer of data.

An block diagram of the transmission of the data is illustrated on FIG. 3.

First, the sensor associated with the head mounted device of the wearer senses at least one wearer's visual behavior data. Such wearer's visual behavior data are sent using the communication unit to the wearer information data generating unit. The wearer information data generating unit generates wearer information data based on the analysis of the wearer's visual behavior data measured over time. The wearer information data generating unit may further use the wearer's visual behavior data and/or the wearer information data to generate a recommendation data.

In an embodiment, the recommendation data may be selected based on technical specifications data of the head mounted device and/or associated devices data such as the number of sensors and/or their sensitivity and accuracy.

The service offer may be provided as a temporary or permanent offer such as an application that could be downloaded in the HMD by the user.

The service offer may be refined based on visual behaviour data learning process and/or optimization of visual behaviour data to be monitored.

The monitoring system according to the invention may be used for research purposes or for wearing tests involving for example a group a users so as to determine, for a specific application and/or program and/or service offer, the most appropriate set of wearer's visual behavior parameters to be monitored and/or the most appropriate head mounted device configuration, and/or the most appropriate sensors to be used. The determination of the most appropriate set of sensors to be used for a specific application may take into consideration, for example, sensor accuracy and/or energy consumption and/or sensor type. Measuring frequencies for each sensor can be optimized depending on energy constraints and/or requirement of the program and/or application.

For example, for early sleepy state detection application, it might be found—after collecting and analyzing over time various wearer's visual behavior data on a group of users—that monitoring blinking frequency in addition to pupil size might provide better results than monitoring pupil size alone.

In an alternative embodiment, the monitoring system according to the invention may be used for "every-day" purposes. The user may for example download an program and/or an application that allows upon the monitoring over time of specific wearer's visual behavior parameters to provide a specific service such as an alert or an indication.

Upon download of said program and/or application an information indicative of the level of compatibility of said program and/or application with respect to the user's specific head mounted device configuration may be provided to the user. For example, the information indicative of the level of compatibility may depend on the type of sensors and/or the degree of accuracy of the sensors and/or the power consumption associated with said specific head mounted device.

Thus, when selecting a specific program and/or application, the user can decide to use and/or download said program and/or application based on said information indicative of the level of compatibility. The download of the program and/or application can be done, for example, on the user's head mounted device and/or one of the user's associated wearable device, like, for example, the wearer's smartphone and/or smart watch.

In an alternative embodiment, the wearer data generating unit 16 may be further configured to send to a printing unit a printing request based on information indicative of the generated wearer information. The printing request causes said printing unit to print a object representative of the generated wearer information.

In an example, the printing unit is an additive manufacturing device making object form 3D model data. By additive manufacturing we mean a manufacturing technology as defined in the international standard ASTM 2792-12, which mentions a process of joining materials to make objects from 3D model data, usually layer upon layer, as opposed to subtractive manufacturing methodologies, such as traditional machining. The additive manufacturing method may be selected in, but is not limited to, the list consisting of stereolithography, mask stereolithography or mask projection stereolithography, polymer jetting, scanning laser sintering or SLS, scanning laser melting or SLM, fused deposition modeling or FDM.

Therefore, the printing request may cause the additive manufacturing device to create an object such as a lens of a spectacle frame or a optical equipment based on the generated wearer information.

In another example, the printing unit is a printer used to print a flyer or advertising paper. The flyer or advertising paper may propose an optical product or service offer based on the generated wearer information.

Figure 4:
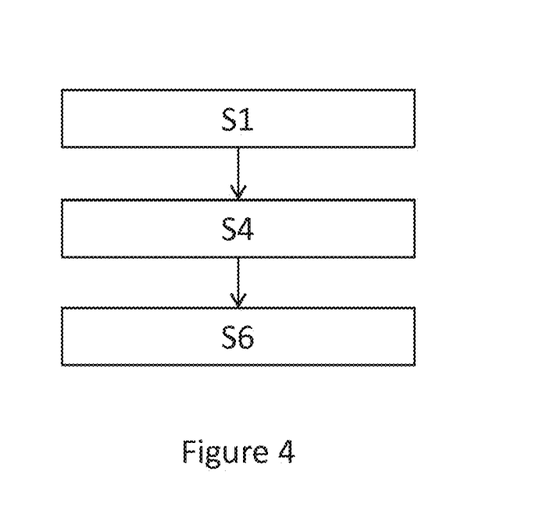
FIG. 4 is an illustration of a chart-flow of a method according to a first embodiment of the invention.

As represented on FIG. 4, the invention further relates to a method for monitoring the vision behavior of a wearer using a monitoring system according to the invention, the method comprises at least:
  a wearer visual behavior data sensing step S1
  a wearer visual behavior data receiving step S4, and
  an information generating step S6.

During the wearer visual behavior data sensing step S1 wearer visual behavior data are sensed and sent to the data generating unit.

During the wearer visual behavior data receiving step S4 the wearer visual behavior data are received by the data generating unit.

The data generating unit generates an information indicative of wearer visual behavior over time based at least on the wearer visual behavior data during the information generating step S6.

The wearer visual behavior data sensing step S1 and the wearer visual behavior data receiving step S4 are repeated over time so as to monitor the visual behavior of a wearer. The frequency of repetition of the wearer visual behavior data sensing step S1 can be optimized depending on energy consumption constraints and/or requirement of the specific application and/or program and/or service offer.

As represented on FIG. 4, the method of the invention may further comprise a recommendation providing step S7 during which the data generating unit provides a recommendation relative to the vision of the wearer. The recommendation being based at least on the information indicative of the evolution of the wearer visual behavior over time.

According to an embodiment of the invention the monitoring system may determine human emotions or affective states of the wearer. For example, the monitoring system may determine fear, joy, love, sadness, surprise, anger or other affective states such as boredom, confusion, delight, flow, frustration etc. . . . and the wearer information data generating unit may provide recommendation data adapted to the affective state of the wearer.

The sensor may typically be, but not limited to, a camera filming part of the wearer's face, such as one or both of the wearer's eye, the region around the wearer's eye.

Standard learning tools, such as Hidden Markow Model, can be used to recognize the emotions/affective states of the wearer.

For example, if the wearer information data generating unit determines fear and/or surprise of the wearer, the service offer provided may be to propose to call emergency team, police and/or one of his close friends. The service offer may be done by oral communication and/or by displaying an image or an hologram. The service offer may be triggered in a substep, after the confirmation of the wearer that something is wrong. The police may also connect to the eyewear via a camera mounted in the eyewear to derive an information relating to the event occurring and find the wearer by his geolocalization.

In another example, if joy and/or delight and/or emotion in front of an advertising, a store, a bill, a magazine are determined by the wearer information data generating unit, the recommendations provided may be the following: referencing the store in its preferences, displaying a proposition of order/purchase of products, sending more detailed information on the advertising, store, bill or magazine. Sending may a email sending and may be replaced by a phone call or a display of information in the HMD or in an hologram in front of the eye of the wearer.

In another example, if joy and/or delight and/or emotion during reading, film, sport or olfactory experience, walk activities are determined, the monitoring system is configured to identify the characteristics generating the emotion (particular words, images, smells, . . . , real scene situations) to generate or fine tune the wearer profile and provide personalized service offers.

The monitoring system according to the invention may be used for early detection of events occurring around the wearer of the head mounted device or affecting the wearer of the head mounted device. In such a case, for example, from the analysis of at least one wearer visual behavior data on a group of wearers such as for example human emotions or affective states of the wearers, it can be derived an information relating to an event occurring in the area where the group of wearer is located. Thus an alert and/or a recommendation and/or a particular service offer can be generated. For example, an alert can be send to the police, optionally including the geolocalization of the group of wearers, the time of the day, the identification of the wearers and the opportunity to the police to check the event occurring based on board camera of the eyewear, if any.

The monitoring system may further be used as an alternative to actual authentication system. Indeed, the visual behavior of a wearer over a period of time in a given visual condition can be used to identify such wearer. The authentication mechanism involves an dynamic visual signature identifier.

Sensors are configured to obtain various type of information regarding the signature characteristic of a user's eye movement and/or patterns of the user's eye movements. One or several eyemovement patterns may be used for providing a user profile for the authorized wearer.

The monitoring system may involve the recognition of eye movements which are unlikely to be intended by the authorized wearer user of the HMD. Upon this recognition, the device may responsively initiate an action to restrict access to the head mounted device and/or information stored thereon, such as locking the head mounted device.

A given wearer may be identified using an eye movement biometric authentication. For example, the wearer may be identified by monitoring the gaze direction combined with several eye parameters, like pupil size, over time while the user is observing a visual stimulus.

During an initial learning phase, for example when using the monitoring system for the first time, the wearer may select the most appropriate visual stimulus among several choice to optimize success rate of authentication and/or usability based on user's feedback.

Advantageously, once the head mounted device has been properly configured, the head mounted device may identify the wearer without requiring any active action from the wearer, just by monitoring the visual behavior of the wearer over time in response to different visual conditions and/or visual stimuli. The visual stimuli can be, for example, a text to be read by the wearer and/or a serie of pictures and/or a movie.

If the wearer behavior over time does not correspond to the expected eye behavior of the wearer, the monitoring system, in particular the wearer information data may generate an alert signal. For example, the head mounted device may be locked until the wearer enters a predetermine pin code in an associated device, such as a smart phone.

Optionally, in addition to visual stimulus, the head mounted device may send authentication request to associated device of the user, such as a smart watch or smart phone, to request authentication for example via a pin code that can be inputed from said associated device of the wearer. This option can be used, for example, to increase the success rate of wearer's authentication.

In order to increase authentication rate and/or usability, in addition to the monitoring of the visual behavior of the wearer, other type of response of the wearer can be also monitored, like for example and not limited to, cerebral response to visual stimuli, vocal signature to visual stimuli . . . .

In case the head mounted device of the wearer is lost or stolen, the wearer may remotely lock the head mounted device by using an associated device such as a smart watch, smart phone or by connecting to a web site to send a blocking instruction to the head mounted device.

The monitoring system may further be used to monitor the health of the wearer.

According to an embodiment of the invention, the wearer's visual behavior sensor may be adapted to determine the oculomotor behavior of the wearer. The oculomotor behavior together with other visual behavior of the wearer, such as the frequency of blinking, the size of the pupil, may be used to monitor the health of the wearer.

For example, the monitoring system according to the invention may be used to determine a sleepy state of the wearer combined with an information on the activity of the wearer, for example an indication that the wearer is driving, the wearer information data generating unit may generate a recommendation data to take a break or even an alert such as a sound alert or vibration alert.

According to an embodiment the head-mounted device further comprises an eye tracking device adapted to track the gazing direction of the wearer. The eye tracking device is well adapted to determine the oculomotor behavior of the wearer that may be included in the visual behavior data sent to the wearer information data generating unit.

According to an embodiment of the invention, the monitoring system further comprises an optical function controller adapted to control the optical function of the head-mounted device. Advantageously, the wearer's visual behavior data or recommendation data may comprise at least one optical parameter of the optical function of the head mounted device. Therefore, the monitoring system may, based on the monitoring of the wearer's visual behavior, adapt or suggest to adapt the optical function of the head mounted device.

The optical function may comprise dioptric function, light absorption, polarizing capability, reinforcement of contrast capacity, etc. . . .

The dioptric function corresponds to the optical lens power (mean power, astigmatism etc. . . . ) as a function of the gaze direction.

The optical function of the head mounted device may comprise the dioptric function of at least one the lenses that the head mounted device may comprise, a sun protection function for example by controlling a transmission parameter of the head mounted device or the polarization of a surface of at least one of the lenses that the head mounted device may comprise.

According to an embodiment, the head mounted device comprises a camera adapted to acquire images of the environment of the wearer and a display device adapted to display to the wearer virtual images in addition to the real scene seen through the head mounted device. The virtual images correspond to the images acquired by the camera.

According to such embodiment, the optical parameter may comprise at least one parameter relating to the image processing applied to the images acquired by the camera prior to being displayed to the wearer.

Advantageously, having the head mounted device equipped with a sensor adapted to measure an environment parameter may increase the adequacy of the recommendation data provided by the wearer information data generating unit.

For example, by sensing the brightness of the environment of the wearer together with the visual behavior of the wearer, the wearer information data generating unit may determine that the wearer is bothered by the ambient brightness and therefore recommend to adapt the transmission parameter of the head mounted device so as to filter more the ambient light.

The invention further relates to a method of monitoring the vision of a wearer of a head mounted device. The head mounted device comprises at least one sensor adapted to measure at least one visual environment parameter of the visual environment of the wearer. The visual environment parameter may relate to the brightness of the environment of the wearer or the distance of the surrounding objects or the type of activities carried out by the wearer. In case the head mounted device is adapted to display information to the user, the parameters of such display brightness, size, font, contrast, luminosity of the virtual image versus the real world scene etc. . . . may be considered as part of the visual environment of the wearer.

The head mounted device further comprises an optical function controller adapted to control the optical function of the head-mounted device.

Figure 5:
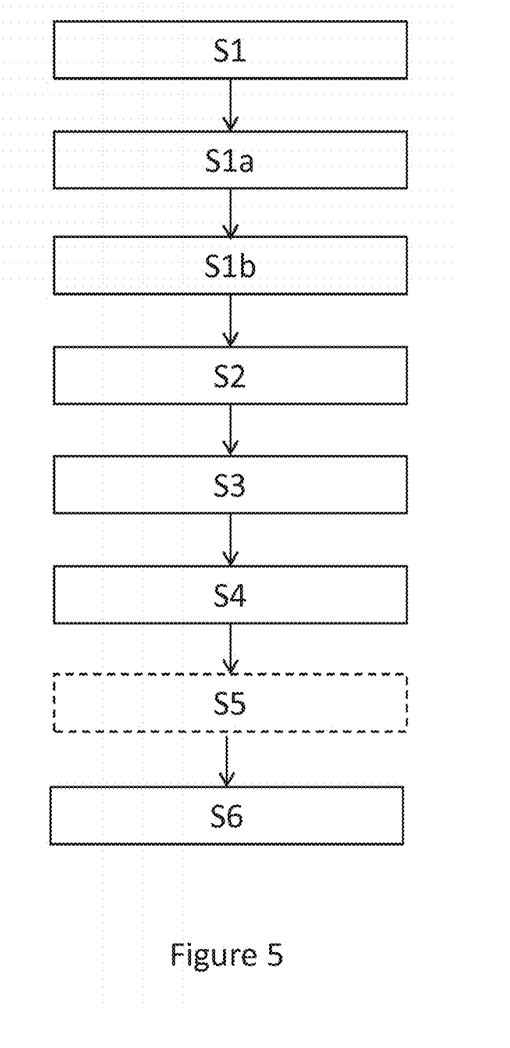
FIG. 5 is an illustration of a chart-flow of a method according to a second embodiment of the invention.

As illustrated on FIG. 5, the method for monitoring the vision of the wearer may comprise:
a wearer visual behavior data sensing step S1,
a visual environment parameter measuring step S2,
a referential optical parameter determining step S3,
a wearer visual behavior data receiving step S4, and
an information generating step S6.

During the wearer visual behavior data sensing step S1, wearer visual behavior data are sensed and sent to the data generating unit.

The wearer visual behavior data sensing step S1 may comprise:
an optical function adapting substep S1a, and
an optical parameter recording substep S1b.

The optical function of the head mounted device is adapted during the optical function adapting sub step S1a.

The optical parameter defining the optical function of the head mounted device is recorded during the optical parameter recording step S1b.

During the visual environment parameter measuring step S2, at least one visual environment parameter is measured upon the optical function adapting substep S1a.

Based on the wearer data and the at least one environment parameter referential optical parameters are determined during the referential optical parameter determining step S3.

The referential parameters correspond to optimize the optical parameter defining the optimized optical function of the head mounted device based on the wearer data and environment parameters. The wearer data comprise at least the wearer's prescription. Such prescription may correspond to an emmetropic prescription and may comprise a phase portion and an amplitude portion.

Knowing the wearer data and the measured environment parameter the optical function that should theoretically have the head mounted device is determined and defined by the referential optical parameters.

According to a preferred embodiment of the invention, the referential optical parameters are determined by the data generating unit or any other computing entity that may communicate with the head mounted device, such as a smart phone, smart watch, a distant server etc. . . .

The wearer parameters are sent to the data generating unit during the wearer visual behavior data receiving step S4.

During the information generating step S6, the data generating unit generates an information indicative of wearer visual behavior over time based at least on the wearer visual behavior data. Furthermore, the data generating unit may check the evolution over time of the difference between the referential parameters and the actual optical parameters of the head mounted device.

Indeed, a drift between the referential optical parameters and the actual optical parameters, for example set by the wearer, may indicate a change of the vision of the wearer.

According to an embodiment of the invention, the method may further comprise a alert step S5, during which an alert is trigged when the difference between the referential optical and the optical parameter is greater than a threshold value.

The threshold value may be set according, but not limited, to the wearer and/or the optical parameter and/or the visual ability or disease of the wearer.

According to an embodiment of the invention, the head mounted device may comprise a camera adapted to acquire images of the environment of the wearer and a display device adapted to provide to a user virtual images in addition to the real scene seen through the head mounted device, the virtual images depending on the images acquired by the camera, wherein during the optical function adapting step an image processing is applied to the virtual images depending on the images acquired by the camera prior to being displayed to the wearer.

According to such embodiment, the optical parameter may relate to the luminosity of the display device and the visual environment parameter relates to the luminosity of the visual environment.

Typically the image processing may comprise at least a magnification processing allowing the wearer to zoom in or out on the virtual image. Comparing the use of the magnification processing by the wearer with the theoretical use of such magnification provides indication on a change of vision of the wearer. For example, if the wearer systematically zooms in the virtual image more than the referential zoom, an alert or recommendation may be generate to inform the wearer or his eye care professional of a probable change of the wearer vision.

The referential zoom may be obtain either by theoretical calculation based on information on the wearer vision at a given time or based on a calibration carried out by the wearer, for example when initializing the head mounted device.

According to further embodiments, the image processing may comprise a contrast enhancement processing and the visual environment parameter may relate to the visual environment contrast.

The image processing may further comprise a color enhancement processing and the visual environment parameter relates to the visual environment color contrast.

Furthermore, the image processing may comprise a detail enhancement processing and the visual environment parameter relates to the visual environment color contrast and luminosity.

According to an embodiment of the invention, the head-mounted device further comprises an eye tracking device adapted to track the gazing direction of the wearer.

The method may further comprise during the wearer visual behavior data sensing step S2, an oculomotor parameter determining step during which a oculomotor parameter relating to the oculomotor behavior of the wearer is determined using the eye tracking device.

The value of the oculomotor parameter may be recorded during a oculomotor parameter. The evolution of the oculomotor parameter is checked overtime.

The oculomotor parameter may comprise fixation stability of the wearer.

Furthermore, the oculomotor may be used to determine the reading speed of the wearer, the evolution of the reading speed of the wearer may then be checked over time.

The invention has been described above with the aid of embodiments without limitation of the general inventive concept as defined in the claims.

Many modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A monitoring system for monitoring the visual behavior of a wearer of a head-mounted device, the monitoring system comprises:
  at least one wearer's visual behavior sensor configured to sense at least one wearer's visual behavior data relating to the visual behavior of the wearer of the head-mounted device;
  a communication unit associated with the at least one wearer's visual behavior sensor and configured to communicate said visual behavior data to a wearer information data generating unit;
  a wearer information data generating unit configured to:
  i) receive said wearer's visual behavior data,
  ii) store said wearer's visual behavior data, and
  iii) generate a wearer information data indicative of at least one of: wearer's vision or general health condition of the wearer or wearer's activity or wearer's authentication based, at least, on the evolution over time of said wearer's visual behavior data; and
  the head-mounted device comprising at least one sensor adapted to measure at least one visual environment parameter of the visual environment of the wearer, and an optical function controller adapted to control the optical function of the head-mounted device, where for at least one optical parameter of the optical function of the head-mounted device:
  i) during a wearer visual behavior data sensing step S1, an optical function adapting substep S1a, during which the optical parameter of the optical function is adapted and an optical parameter recording substep S1b, during which the value of the optical parameter of the optical function is recorded,
  ii) a visual environment parameter measuring step S2, during which at least one visual environment parameter is measured upon the optical function adapting step S1a,
  iii) a referential optical parameter determining step S3, during which a referential optical parameter is determined based on the measured value of the at least one visual environment parameter and wearer data,
  iv) a wearer visual behavior data receiving step S4 during which the wearer visual behavior data are received by the data generating unit,
  v) an information generating step, during which the data generating unit generates the wearer information data indicative of wearer visual behavior over time based at least on the wearer visual behavior data,
  wherein steps S1 to S4 are repeated over time and during the information generating step, the evolution of a difference between the referential optical parameter and the optical parameter is checked over time.

2. The monitoring system according to claim 1, wherein the wearer information data generating unit is configured to generate wearer information data using statistical analysis of said at least one wearer's visual behavior data received and stored over time.

3. The monitoring system according to claim 2, wherein the wearer information data generating unit is a distant entity from the head-mounted device, the wearer information data generating unit being further arranged to communicate with sensors associated to a plurality of head-mounted devices.

4. The monitoring system according to claim 2, wherein the generated wearer information data are indicative of human emotions and/or affective states of the wearer.

5. The monitoring system according to claim 2, wherein the wearer information data generating unit is configured to provide a recommendation data based, at least, on at least one of the wearer's visual behavior data or the generated wearer information data and wherein the recommendation data includes a lens design recommendation and/or an ophthalmic lens recommendation and/or an alert indicative of wearer's vision state and/or an activation of at least one functionality on the head-mounted device and/or an access to a service offer.

6. The monitoring system according to claim 1, wherein the wearer information data generating unit is a distant entity from the head-mounted device, the wearer information data generating unit being further arranged to communicate with sensors associated to a plurality of head-mounted devices.

7. The monitoring system according to claim 6, wherein the information data generating unit is configured to receive wearer's visual behavior data relating to a plurality of wearers and wherein said generated wearer information data is based, at least, on said wearer's visual behavior data relating to a plurality of wearer's.

8. The monitoring system according to claim 7, wherein the generated wearer information data are indicative of human emotions and/or affective states of the wearer.

9. The monitoring system according to claim 6, wherein the generated wearer information data are indicative of human emotions and/or affective states of the wearer.

10. The monitoring system according to claim 1, wherein the generated wearer information data are indicative of human emotions and/or affective states of the wearer.

11. The monitoring system according to claim 1, wherein the wearer information data generating unit is configured to provide a recommendation data based, at least, on at least one of the wearer's visual behavior data or the generated wearer information data and wherein the recommendation data includes a lens design recommendation and/or an ophthalmic lens recommendation and/or an alert indicative of wearer's vision state and/or an activation of at least one functionality on the head-mounted device and/or an access to a service offer.

12. The monitoring system according to according to claim 1, wherein the monitoring system is used for early detection of events occurring around a wearer.

13. The monitoring system according to claim 1, wherein the wearer information data generating unit is arranged to send the wearer information data to a wearable computer device, a personal computer device and/or a smart building device associated to the wearer of the head-mounted device.

14. The monitoring system according to claim 1 further configured to send to a printing unit a printing request based on information indicative of the generated wearer information, and wherein the printing request causes said printing unit to print a object representative of the generated wearer information.

15. The monitoring system according to claim 1, wherein the wearer's visual behavior data comprise head-mounted device use data.

16. A method for monitoring the vision of a wearer using a head-mounted device with a monitoring system that comprises:
at least one wearer's visual behavior sensor configured to sense at least one wearer's visual behavior data relating to the visual behavior of the wearer of the head-mounted device;
a communication unit associated with the at least one wearer's visual behavior sensor and configured to communicate said visual behavior data to a wearer information data generating unit; a wearer information data generating unit configured to:
i) receive said wearer's visual behavior data,
ii) store said wearer's visual behavior data, and
iii) generate a wearer information data indicative of at least one of: wearer's vision or general health condition of the wearer or wearer's activity or wearer's authentication based, at least, on the evolution over time of said wearer's visual behavior data, and
wherein the head-mounted device comprises at least one sensor adapted to measure at least one visual environment parameter of the visual environment of the wearer, and an optical function controller adapted to control the optical function of the head-mounted device, the method comprising:
a wearer visual behavior data sensing step S1 during which wearer visual behavior data are sensed and sent to the data generating unit;
a wearer visual behavior data receiving step S4 during which wearer visual behavior data are received by the data generating unit;
an information generating step, during which the data generating unit generates an information indicative of wearer visual behavior over time based at least on the wearer visual behavior data,
wherein the wearer visual behavior data sensing step S1 and the wearer visual behavior data receiving step S4 are repeated over time; and
for at least one optical parameter of the optical function of the head-mounted device:
i) during the wearer visual behavior data sensing step S1, an optical function adapting substep S1a, during which the optical parameter of the optical function is adapted and an optical parameter recording substep S1b, during which the value of the optical parameter of the optical function is recorded,
ii) a visual environment parameter measuring step S2, during which at least one visual environment parameter is measured upon the optical function adapting step S1a, and
iii) a referential optical parameter determining step S3, during which a referential optical parameter is determined based on the measured value of the at least one visual environment parameter and wearer data,
wherein steps S1 to S4 are repeated over time and during the information generating step, the evolution of a difference between the referential optical parameter and the optical parameter is checked over time.

17. The method according to claim 16, wherein the head-mounted device comprises a camera adapted to acquire images of the environment of the wearer and a display device adapted to provide to a user virtual images in addition to the real scene seen through the head-mounted device, the virtual images depending on the images acquired by the camera, wherein during the optical function adapting step an image processing is applied to the virtual images prior to being displayed to the wearer.

18. The method according to claim 16, wherein the head-mounted device further comprises an eye tracking device adapted to track the gazing direction of the wearer, and wherein the method further comprises:
during the wearer visual behavior data sensing step S2, an oculomotor parameter determining step during which an oculomotor parameter relating to the oculomotor behavior of the wearer is determined using the eye tracking device, and
an oculomotor parameter recording step during which the value of the oculomotor parameter is recording,
and during the indication of wearer visual behavior evolution over time generating step, the evolution of the oculomotor parameter is checked over time.

19. The method according to claim 16, wherein during the optical function adapting step S1, the transmission of the head-mounted device is adapted and the visual environment parameter measuring during the visual environment parameter measuring step S3 corresponds to the light spectrum and/or light intensity of the visual environment.

* * * * *